United States Patent
Re

(10) Patent No.: US 6,187,818 B1
(45) Date of Patent: Feb. 13, 2001

(54) PROSTAGLANDINS FORMULATION AND PROCESS

(75) Inventor: Robert G. Re, Portage, MI (US)

(73) Assignee: Pharmacia & Upjohn Company, Kalamazoo, MI (US)

(*) Notice: Under 35 U.S.C. 154(b), the term of this patent shall be extended for 0 days.

(21) Appl. No.: 09/094,985

(22) Filed: Jun. 17, 1998

(51) Int. Cl.$^7$ .................................................. A61K 31/19
(52) U.S. Cl. ........................................... 514/573; 514/559
(58) Field of Search .................................. 514/573, 559; 424/318

(56) References Cited

U.S. PATENT DOCUMENTS

| | | | |
|---|---|---|---|
| 3,885,041 | * 5/1975 | Aspinall et al. | 424/318 |
| 3,903,297 | 9/1975 | Robert | 424/318 |
| 3,917,864 | 11/1975 | Karim | 424/305 |

FOREIGN PATENT DOCUMENTS

| | | |
|---|---|---|
| 0 268 066 | 10/1987 | (EP). |
| WO 98/41208 | 3/1998 | (WO). |

OTHER PUBLICATIONS

Martindale The Extra Pharmacopocia, 28 ed., Editor James EF Reynolds, The Pharmaceutical Press, London P.P. 1355–1357, 1982.*

Hamberg, M., et al., *Eur. J. Pharm. Sci.*, 3(1) pp. 27–38 (1995).

* cited by examiner

*Primary Examiner*—F. T. Moezie
(74) *Attorney, Agent, or Firm*—Thomas A. Wootton; Andrew M. Solomon

(57) ABSTRACT

This invention comprises new formulations and methods of preparing a new formulations of prostaglandins and in particular dinoprost tromethamine, where the pH of the formulation is adjusted to between about 5.5–7.5 and where the the concentration of benzyl alcohol is between about 1.2 to 2.0 mg/ml.

33 Claims, No Drawings

US 6,187,818 B1

PROSTAGLANDINS FORMULATION AND PROCESS

FIELD OF THE INVENTION

This invention relates to the manufacture of an improved formulation for prostaglandins such as dinoprost tromethamine, a compound marketed under the trademark Lutalyse®.

BACKGROUND OF THE INVENTION

Dinoprost tromethamine, a compound marketed under the trademark Lutalyse®, is described and claimed in U.S. Pat. No. 3,917,864 (incorporated herein by reference). When properly administered this compound is able to induce regression of the corpora lutea of many mammals, especially farm animals such as horses, cows and pigs. The active ingredient is frequently formulated as a solution intended for administration by injection. Here we present a surprising and new formulation of dinoprost tromethamine solution for injection that provides advantages over currently available formulations. This new method of formulation appears suitable for dinoprost tromethamine and other prostaglandin drugs.

SUMMARY OF THE INVENTION

This invention comprises new formulations, both as compositions per se and as products by process as well as new procedures for making those formulations. The formulations include, a solution comprising a prostaglandin such as dinoprost tromethamine and benzyl alcohol, the benzyl alcohol may be between about 1.2 to 2.0%, the entire solution is adjusted to a pH of between about 5.5–7.5, or more preferred to a pH of between about 6–7 and most preferred is between about 6.4–6.6, or about 6.5. The concentration of dinoprost tromethamine may be 1–10 mg/ml, preferably it is 3–7 mg/ml and more preferably it is 5 mg/ml. The concentration of benzyl alcohol may be between about 12–20 mg/ml and the concentration of dinoprost tromethamine may be between about 4–6 mg/ml. Preferably the concentration of dinoprost tromethamine is about 5 mg/ml and the concentration of benzyl alcohol is about 16.5 mg/ml in the final solution. The solution may be adjusted to a pH of about 6.5 or 6.6.

Also disclosed is a product made by a particular process. A solution of prostaglandin and benzyl alcohol adjusted to a pH of between about 5.5–7.5, more preferred is between about 6–7 and most preferred is between about 6.4–6.7, or about 6.5, where the concentration of benzyl alcohol is between about 1.2 to 2%, more preferred is 1.4 to 1.8%, with the most preferred being 1.65% and where the concentration of dinoprost tromethamine is 1–10 mg/ml., made by the process of either a) dissolving dinoprost tromethamine in water and then adding diluted benzyl alcohol or diluting benzyl alcohol and adding the dinoprost to the benzyl alcohol water solution (where diluted benzyl alcohol may be a solution of between about 4 and 1.2% benzyl alcohol, more preferred is 1.2–3.3%, even more preferred is 1.8 to 2.6% and most preferred is a 2.0% solution of benzyl alcohol, or b) by dissolving dinoprost in one vessel and dissolving benzyl alcohol in water in another vessel, using a solution of benzyl alcohol between about 4.0%–1.2%, more preferred is 1.2–3.3%, even more preferred is 1.8 to 2.6% and most preferred is a 2.0% solution of benzyl alcohol, followed by mixing the contents of the two vessels. This is followed by adjusting the pH to between about 5.5 and 7.5 or more preferably between about 6 and 7 with a weak acid or base, and if needed with a final pH adjustment of between 5.5–7.5, or better between about 6–7 or even better right at about 6.5. The prostaglandin formulated by this process may be dinoprost tromethamine. In this process the pH of the benzyl alcohol water solution may be adjusted to between 5.5–7.5 before or after it is mixed with the dinoprost tromethamine in water solution. The pH may be adjusted with an acid or base such as HCl or NaOH. The final concentration of benzyl alcohol can be between about 1.2 and 2.0% or more preferred is between about 1.4 and 1.8%, even more preferred is between about 1.6–1.7% or about 1.65% which is also about 16.5 mg/ml of benzyl alcohol in water in the final solution.

Also disclosed is a process for preparing a pharmaceutical formulation of a prostaglandin comprising: either I) dissolving the prostaglandin in water first and then adding benzyl alcohol or II) diluting benzyl alcohol in water to a solution of about 4% or less and then adding the prostaglandin. If the former procedure is used, it may be done by a) dissolving dinoprost tromethamine in water and adding diluted (solution of 4% to 1.2% benzyl alcohol) and adjusting the pH to between about 5.5.–7.5, or 6–7 or about 6.5 or b) dissolving dinoprost tromethamine in water in one vessel and dissolving benzyl alcohol in water in another vessel, followed by mixing the contents of the two vessels together and adjusting the pH to between about 5.5.–7.5, or about 6.0–7.0 or about 6.5 with a weak acid or base. The prostagladin can be dinoprost tromethamine. The concentration of benzyl alcohol in this process can be between about 1.2 to 2.0%, or 1.4–1.8%, 1.5–1.7%, 1.6–1.7%, preferably it is 1.65% or 16.5 mg/ml.

A different but related procedure may be used where the dinoprost is added to water and then the pH is raised to pH 8.0 or above, then benzyl alcohol is added (either pure or diluted benzyl alcohol) and then the pH is lowered to between about 5.5.–7.5, or 6–7 or about 6.5 with a weak acid or base The concentration of dinoprost tromethamine is 1–10 mg/ml in the process, preferably 3–7 mg/ml, more preferably it is 4–6 mg/ml and even more preferably 5 mg/ml. In this process the pH may be adjusted in the benzyl alcohol water solution both after the benzyl alcohol is mixed with the water but before the dinoprost tromethamine water solution is added to the benzyl alcohol water solution and/or after the the benzyl alcohol water solution is added to the dinoprost tromethamine water solution or the pH may be adjusted either before or after the benzyl alcohol in water solution is made and before or after the dinoprost is added to the diluted alcohol water solution if that procedure is used and with either of these procedures, the final pH may be adjusted to between about pH 5.5–7.5 or more preferably 6.0 or 7.0, or more preferred between about 6.4–6.6 or about 6.5 for either or both pH adjustments. The concentration of benzyl alcohol in this process can be between about 1.2 to 2.0%, or 1.4–1.8%, 1.5–1.7%, 1.6–1.7%, preferably it is about 1.65% or 16.5 mg/ml.

ADDITIONAL DESCRIPTION OF THE INVENTION

Dinoprost tromethamine is a type of prostaglandin, see U.S. Pat. No. 3,917,864, incorporated by reference. Prior to this invention it was widely believed that most prostaglandins, and dinoprost tromethamine in particular, needed to be formulated into an alkaline solution in order to produce chemically and physically stable solutions of the drug. For example see, Mats Hamberg, Lian-Ying Zhang, Sune Bergstroem, "On the pH-dependent degradation of 15(S)-15 methyl-prostaglandin F2 alpha (Carboprost)" *Eur. J. Pharm. Sci.,* 3(1), 27–38 (English) 1995. This study found a gradual increase in stability of a tromethamine salt of a prostaglandin when the pH values of the buffers used were increased from 9.1 to higher and concluded that the drug could be stored for at least a year with only 3–4% degradation when maintained at 37 degree provided the buffer was maintained at pH 9.55. The study is typical of what was believed about prostaglandins, that they were more stable when maintained at a higher pH. The inventors here have discovered a new method of making a new formulation of dinoprost tromethamine that no longer requires an alkaline formulation. The elimination of the alkaline normally used to keep dinoprost tromethamine and other prostaglandins chemically stable and in solution may even allow for an injectable formulation with fewer injection site complications than a high pH solution.

In addition to these important pH related improvements to this new formulation and method of manufacture of prostaglandins the inventors have discovered a novel method of producing an injectable solution that is superior at decreasing microbial contamination of the solution. The inventors here have created a novel method of producing a sterile solution of dinoprost tromethamine that contains a high concentration benzyl alcohol and yet remains a clear solution. Typically with the levels of benzyl alcohol and pH used here one would expect the prostaglandin to fall out of solution and form a precipitation; yet because of the unique manner of formulation, formulations suitable for storage and injection, the formulations produced here are true solutions, clear and containing dissolved drug, not precipitates.

A scientist making an injectable prostaglandin drug formulation faces many hurtles. First, as mentioned above, prostaglandin drugs are typically more stable at higher pH. As pH is decreased two principle undesirable affects occur. The prostaglandin drug becomes unstable and progressively degrades chemically and it physically precipitates out of solution. Below a pH of about 6 most prostaglandin drugs, such as dinoprost tromethamine, are not stable in liquid solutions. Unfortunately, raising the pH presents other problems. Injectible drug solutions are subject to microbial growth and contamination when the solutions are utilized as multi-use vials. The repeated insertion and withdrawal of needles into drug for injection sometimes allows contaminates to enter the drug vial. The addition of preservatives such as benzyl alcohol are often added to such solutions to inhibit microbial growth resulting from possible contamination. Unfortunately, the inhibitory effect of benzyl alcohol on microbial growth is itself inhibited at higher pH. As the pH of a solution containing benzyl alcohol is increased the growth of microbial organisms in that solution also increases. The prostaglandin drug formulator is thus presented with the Hobson's choice of either high pH with good drug stability but greater chance of contamination and drug precipitation or a lower pH with better inhibition of microbial contamination but a short period of chemical stability or shelf life.

If one begins with a standard solution of pH 8 or so and a typical benzyl alcohol concentration of about 9 or 10 mg/ml, usually sufficient to prevent microbial growth, or achieve desired lethality, merely lowering the pH will not produce a suitable pharmaceutical formulation. Because of microbial challenge the benzyl alcohol level must be increased at higher pHs; however, the manner in which the concentration of benzyl alcohol is raised is critical in order to keep the prostaglandin, such as dinoprost tromethamine, in solution.

The inventors here have discovered and now disclose the secret of making prostaglandin formulation in a non-alkaline environment which allows for clear solutions of stable drug with an optional formulation having effective levels of benzyl alcohol.

Prostaglandin formulations can be made in non-alkaline environments which contain benzyl alcohol, provided the benzyl alcohol is raised to a higher than typical concentration and provided that the order of mixing the ingredients is as disclosed here.

Typically in formulating solutions the addition of the least soluble ingredients are placed into solution first with the more soluble ingredients added last. Here we change the typical procedure in order to keep the dinoprost tromethamine in solution. If the dinoprost tromethamine is added to the water followed by the addition of straight benzyl alcohol the dinoprost tromethamine will precipitate out of solution. Here we teach the dissolution of the dinoprost tromethamine in water followed by adding a solution of benzyl alcohol dissolved in water. Alternatively, the benzyl alcohol may be dissolved in water followed by the dissolution of the dinoprost tromethamine in the dilute benzyl alcohol solution. Benzyl alcohol has a solubility of about 4% in water. Any solution of benzyl alcohol should be acceptable and it is possible that emulsions of 5, 6, 7, 8, 9 or 10% benzyl alcohol are also acceptable. We prefer diluted benzyl alcohol (where diluted benzyl alcohol may be a solution of between about 4 and 1.2% benzyl alcohol, more preferred is 1.2–3.3%, even more preferred is 1.8 to 2.6% and most preferred is a 2.0% solution of benzyl alcohol, or b) by dissolving dinoprost in one vessel and dissolving benzyl alcohol in water in another vessel, using a solution of between about 4.0%–1.2%, more preferred is about 1.2–3.3%, even more preferred is about 1.8 to 2.6% and most preferred is about 2.0% solution of benzyl alcohol. The final pH is adjusted to between about 5.5–7.7, 6.0–7.0 or 6.5. This can be accomplished in one vessel or two using any of the following procedures.

We describe several general procedures.

I) A prostaglandin, such as dinoprost tromethamine and appropriate amounts of diluted (about 4 to 1.2%) benzyl alcohol are first dissolved in water, note, either the benzyl alcohol may be added to the water first, or the prostaglandin may be added first; and then the pH is adjusted with an appropriate acid or base, such as mineral acid or bases like hydrochloric acid (HCl) or sodium hydroxide (NaOH), or organic acids or bases.

II) One may first dissolve the dinoprost tromethamine in water in one vessel and dilute the benzyl alcohol with water in another vessel. The vessels are mixed and the pH is adjusted again to about between about 5.5–7.7, 6–7 or 6.5, water is added to obtain the final size and the solution is mixed.

III) Alternatively the prostaglandin can be dissolved in water and the pH raised to about a pH of about 8.0, preferably higher, (or the pH is raised before the prostaglandin is added) then undiluted (straight) or diluted benzyl alcohol is added before the pH is lowered. To repeat, with this alternative method III one should raise the pH after the prostaglandin is dissolved and then add either straight or diluted benzyl alcohol, following this the pH is lowered to the range of about 5.5–7.5, more preferably about 6–7 or most preferably about 6.5. The preferred prostaglandin is dinoprost tromethamine.

For any of the procedures above it is preferred that the final benzyl alcohol concentration is in the concentration range of 1.2% to 2.0% w/v with more preferred from 1.4 to 1.8% with the most preferred being about 1.65% or where each ml final volume of formula contains 5 mg of dinoprost tromethamine and 16–17 mg of benzyl alcohol, more preferred is 16.5 mgs mixed into each ml. water with a pH adjustment using solutions of either HCl or NaOH. Any acid solution may be used, a 1–10% solution of acid or base works well. A higher concentration may be desired for larger volumes. For larger solutions one can mix 4.0 kg of dinoprost tromethamine and 13.2 kg of benzyl alcohol to a solution of water with a pH adjustment using 10% solutions of either HCl or NaOH and bringing the final aqueous volume to 800 liters.

The pH range that is suitable for this invention is from pH about 5.5–7.5, with a pH about 6.0–7.0 preferred, with a pH of 6.5 or 6.6 most preferred.

The concentration of dinoprost tromethamine may be 1–10 mg/ml, preferably it is 3–7 mg/ml, more preferably it is 4–6 mg/ml and even more preferably it is 5 mg/ml.

The final benzyl alcohol range is from 1.2% to 2.0% w/v (weight/volume) or about 12 to 20 mg/ml with 14–18 mg/ml preferred and about 16–17 mg/ml more preferred or about 16.5 mg/ml most preferred. The benzyl alcohol concentration used to make the final solution is a solution of between about 4 and 1.2% benzyl alcohol, more preferred is 1.2–3.3%, even more preferred is 1.8 to 2.6% and most preferred is a 2.0% solution of benzyl alcohol.

From the information provided above one skilled in the art should be able to practice all aspects of this invention. The following specific examples are intended to illustrate and not limit the disclosure of this invention.

SPECIFIC EXAMPLES AND EMBODIMENTS OF THE INVENTION

The required amounts of dinoprost tromethamine and benzyl alcohol are dissolved in Water for Injections. Water for Injection means a water solution suitable for injection, according to the United States Pharmacopia (U.S.P). The pH is adjusted with Sodium Hydroxide or Hydrochloric Acid Solution. The solution is sterilized by filtration through a sterilizing grade membrane filter and aseptically filled through an in-line filter into vials. The containers are sterilized and depyrogenated by dry heat.

The cycle parameters are set to give a minimum process lethality equivalent to a log 3 reduction of the original endotoxin concentration. The rubber closures are sterilized by steam sterilisation. The cycle parameters are set to give a minimum process lethality equivalent to a log 6 reduction of the original spore concentration and a minimum F0 value of 15 minutes.

Charts are provided on the following pages to give a better visual description of the processes and procedures described above. The Charts provide additional description and should not be viewed as limiting the above descriptions.

Chart 1

The following Chart is provided to describe one possible manner of mixing the formulation. Below is a flow diagram of the formulation process.

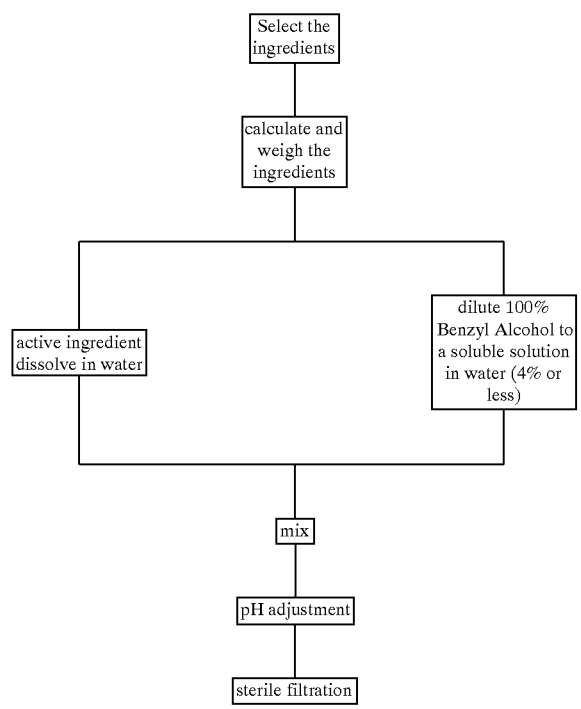

Chart 2a

The following Chart is provided to describe one possible manner of mixing the formulation. Below is a flow diagram of the formulation process.

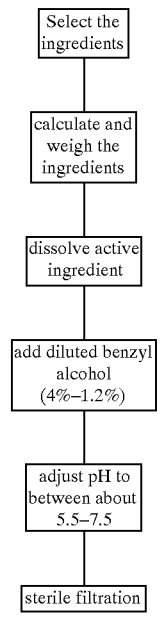

Chart 2b

The following Chart is provided to describe one possible manner of mixing the formulation. Below is a flow diagram of the formulation process

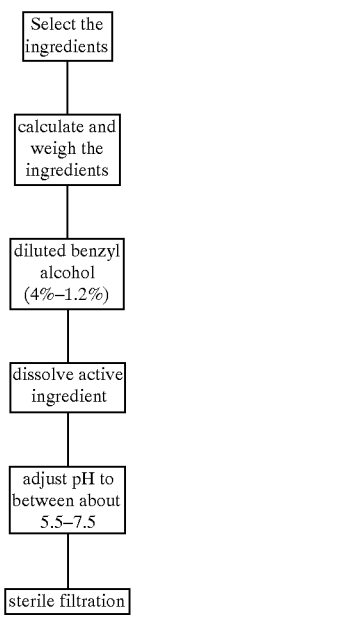

Chart 3

The following Chart is provided to describe one possible manner of mixing the formulation. Below is a flow diagram of the formulation process.

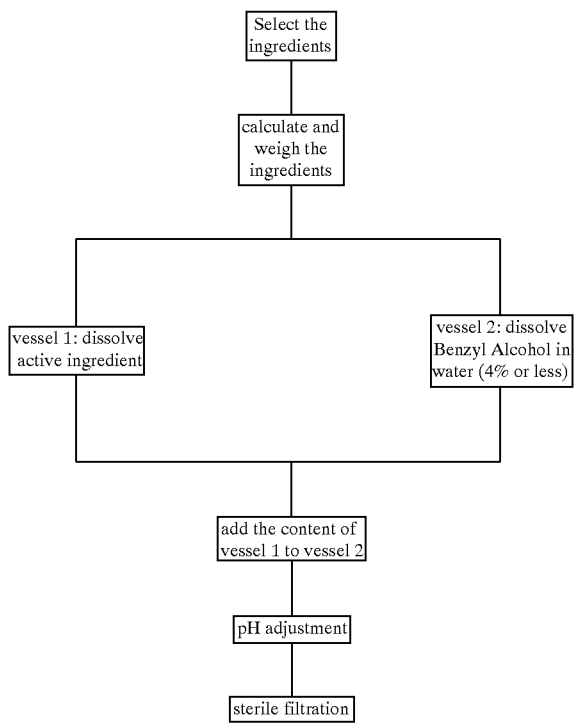

Chart 4

The following Chart is provided to describe one possible manner of mixing the formulation. Below is a flow diagram of the formulation process.

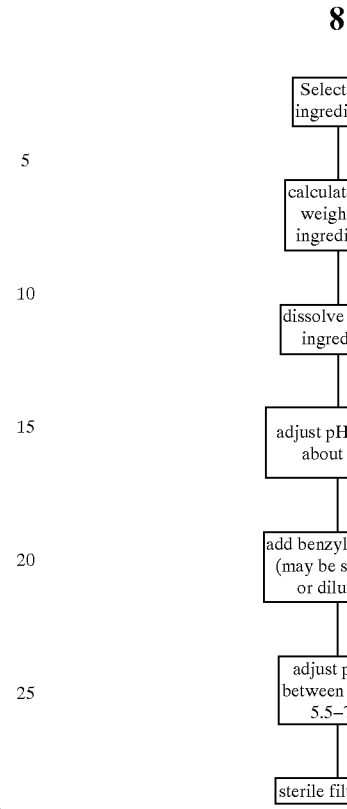

DETAILED DESCRIPTION OF VARIOUS STAGES OF PREPARATION OF THE FORMULATION

Select and weigh the ingredients needed for formulation: benzyl alcohol and dinoprost tromethamine. Calculate the amount of Dinoprost Tromethamine needed from the formula: Quantity needed=A/B, A=quantity of activity needed, B=the actual potency of the lot dinoprost tromethamine/100.

For a lot of 50.0 kg, 250 gram Dinoprost activity is needed which is equivalent to 335.5 gram of dinoprost tromethamine (if it has 100% as potency result). Using a lot of dinoprost tromethamine with a potency of 98.0%, the calculated amount needed is: 335.5/0.98=342.35 gram dinoprost tromethamine.

Select two preparation vessels and the weighed ingredients. To vessel one add about 10 liters of Water for Injections. Add the calculated and weighed amount of dinoprost tromethamine and mix. To vessel two add about 35 liters of Water for Injections.

Add the required amount of benzyl alcohol and mix. Adjust the pH using 1% solution of Hydrochloric Acid and/or 1% solution Sodium Hydroxide to adjust to pH=6.5.

Transfer the content of vessel one to vessel two and mix. Adjust the pH using 1% solution of Hydrochloric Acid and/or 1% solution Sodium Hydroxide toadjust to pH=6.6. Add Water for Injections to obtain the final size and mix, readjusting the final pH if necessary.

With an actual formulation the following additional procedures may also be taken A sample may be drawn for Bioburden testing, as required, the solution can be filtered through a sterilizing membrane filter, for example of 0.22 micron filter may be used, into a sterile vessel. The solution can be sterilized by filtration through a sterilizing membrane filter and aseptically filled through an in-line filter into vials. The containers may be sterilized and depyrogenated by dry heat. The cycle parameters may be set to give a minimum process lethality equivalent to a log 3 reduction of the original endotoxin concentration. The rubber closures may be sterilized by steam sterilisation. The cycle parameters may be set to give a minimum process lethality equivalent to a log 6 reduction of the original spore concentration and a minimum F0 value of 15 minutes. Draw samples at regular times for fill weight. Close the vials with the sterile stoppers and seal with the caps. Draw samples for analysis.

Other Considerations

The following considerations are noted. The pH of the bulk solution prior to filtration may be adjusted with dilute solutions of acid or base like hydrochloric acid or sodium hydroxide. In-process samples can be taken from the top and bottom of the fluids preparation tank at 5, 10 and 15 minutes after the addition of the benzyl alcohol to the Water for Injection to confirm its uniform dissolution prior to the addition of the active component, dinoprost tromethamine. After the addition of the dinoprost solution to the benzyl alcohol solution and solution is brought to volume, samples may be taken from the top and bottom of the fluids preparation tank after 15 and 25 minutes of mixing to confirm both potency and uniformity.

Scientific studies have shown that the procedures described herein produce formulations having acceptable levels of preservative efficacy as determined by both the European Union Pharmacopoeia and the United States Pharmacopoeia.

What is claimed is:

1. An injectable pharmaceutical solution comprising a prostaglandin and benzyl alcohol; said solution having a pH of between about 5.5–7.5 and containing a minimum concentration of benzyl alcohol of 1.2% (w/v).

2. A solution of claim 1 where the prostaglandin is dinoprost tromethamine.

3. A solution of claim 2 where the concentration of benzyl alcohol is between about 1.2 to 2.0% (w/v) or about 12–20 mg/ml.

4. A solution of claim 3 where the concentration of dinoprost tromethamine is 1–10 mg/ml.

5. A solution of claim 2 where the concentration of benzyl alcohol is between about 1.4–1.8% and the concentration of dinoprost tromethamine is between about 4–6 mg/ml.

6. A solution of claim 5 where the concentration of dinoprost tromethamine is about 5 mg/ml and the concentration of benzyl alcohol is about 16.5 mg/ml in the final solution.

7. A solution of claim 6 where the pH is adjusted to about 6.5 or 6.6.

8. A composition comprising a solution of prostaglandin and benzyl alcohol having a pH of between about 5.5–7.5, where the final concentration of benzyl alcohol is between about 1.2 to 2.0% (12–20 mg/ml), and where the concentration of prostaglandin is 1–10 mg/ml, made by the process of dissolving the solutions in water 1) prostaglandin and 2) benzyl alcohol combining a solution and adjusting the pH of the combined solution to between about 5.5 and 7.5 with an acid or base.

9. The solution of claim 8 where the prostaglandin is dissolved in water before the benzyl alcohol is added, and where the initial benzyl alcohol is diluted with water to a concentration of between about 1.2% to 4.0%, before it is added to the prostaglandin water solution.

10. The solution of claim 9, where the prostaglandin is dinoprost tromethamine.

11. The solution of claim 10, where the initial benzyl alcohol is diluted with water to a concentration of between about 1.2 and 3.3% and the benzyl alcohol is adjusted to a final concentration of between about 1.4 to 1.8% (14–18 mg/ml), where the pH is adjusted to between about 6.0 and 7.0 and where the concentration of dinoprost tromethamine is between 4–6 mg/ml.

12. The solution of claim 11, where the initial benzyl alcohol is diluted with water to a concentration of between about 1.8 and 2.6% and the pH is adjusted with HCl or NaOH and the benzyl alcohol is adjusted to a final concentration of between about 1.6 to 1.7% (16–17 mg/ml).

13. The solution of claim 12 where the initial benzyl alcohol is diluted with water to a concentration of about 2.0% and the final concentration of benzyl alcohol is about 1.65% (16.5 mg/ml) of water in the final solution.

14. The solution of claim 8 where the benzyl alcohol is first added to the water to dilute it to between about 4% to 1.2%, and the prostaglandin is then dissolved in the benzyl alcohol water mixture.

15. The solution of claim 14 where the prostaglandin is dinoprost tromethamine.

16. The solution of claim 15, where the initial benzyl alcohol is diluted with water to a concentration of between about 1.2 and 3.3% and the benzyl alcohol is adjusted to a final concentration of between about 1.4 to 1.8% (14–18 mg/ml), where the pH is adjusted to between about 6.0 and 7.0 and where the concentration of dinoprost tromethamine is between about 4–6 mg/ml.

17. The solution of claim 16, where the initial benzyl alcohol is diluted with water to a concentration of between about 1.8 and 2.6% and the pH is adjusted with HCl or NaOH and the benzyl alcohol is adjusted to a final concentration of between about 1.6 to 1.7% (16–17 mg/ml).

18. The solution of claim 8 where: (1) the prostaglandin is dissolved in water and; (2) benzyl alcohol is dissolved in water or distributed in water to form an emulsion of up to 10% benzyl alcohol; and (1) and (2) are combined.

19. The solution of claim 18 where the prostaglandin is dinoprost tromethamine.

20. The solution of claim 19 where the benzyl alcohol separately dissolved in water has a concentration of between about 1.8 and 2.6% and the benzyl alcohol in the combined solution is adjusted to a final concentration of between about 1.4 to 1.8% 14–18 mg/ml), where the pH in the combined solution is adjusted to between about 6.0 and 7.0 and where the concentration of dinoprost tromethamine in the combined solution is between about 4–6 mg/ml.

21. The solution of claim 20, where the acid or base is weak HCl or NaOH and the benzyl alcohol is adjusted to a final concentration of between about 1.6 to 1.7% (16–17 mg/ml).

22. The solution of claim 21 where the pH of the benzyl alcohol water solution is adjusted to between about 6 and 7 before it is mixed with the dinoprost tromethamine in water solution.

23. A process for preparation of a pharmaceutical formulation of a prostaglandin comprising: dissolving the prostaglandin in water and dissolving benzyl alcohol in water, combining the prostaglandin in water and benzyl alcohol in water, and adjusting the pH to between about 5.5 and 7.5 with an acid or base and where the final benzyl alcohol solution is between about 1.2 to 2.0% (12–20 mg/ml) and where the prostaglandin concentration is 1–10 mg/ml.

24. The process of claim 23, where the prostaglandin is dissolved in water before the benzyl alcohol is added, and where the benzyl alcohol is diluted with water to a concentration of between about 4.0 and 1.2%, before it is added to the prostaglandin water solution.

25. The process of claim 24, where the prostaglandin is dinoprost tromethamine.

26. The process of claim 25, where the benzyl alcohol is diluted with water to a concentration of between about 3.3–1.2%, and the final benzyl alcohol concentration is adjusted to between about 1.4 to 1.8% (14–18 mg/ml), where the pH is adjusted to between about 6.0 and 7.0 and where the concentration of dinoprost tromethamine is between 4–6 mg/ml.

27. The process of claim 26, where the benzyl alcohol is diluted with water to a concentration of between about 2.6–1.8%, the pH is adjusted with HCl or NaOH and the benzyl alcohol is adjusted to a final concentration of between about 1.6 to 1.7% (16–17 mg/ml).

28. The process of claim 27 where the benzyl alcohol is diluted with water to a concentration of about 2.0%, and the final concentration of benzyl alcohol is about 1.65% (16.5 mg/ml) of water in the final solution.

29. The process of claim 28 where the benzyl alcohol is added to the water to dilute it to either an emulsion of 4 to 10% or a solution of between about 4 to 1.2% before the prostaglandin is dissolved in the benzyl alcohol water mixture.

30. The process of claim 23 where the prostaglandin is dinoprost tromethamine.

31. The process of claim 30 where the benzyl alcohol is diluted with water to a concentration of between about 3.3–1.2%, the benzyl alcohol in the combined solution is adjusted to a final concentration of between about (1.4 to 1.8% 14–18 mg/ml), where the pH in the combined solution is adjusted to between about 6.0 and 7.0 and where the concentration of dinoprost tromethamine in the combined solution is between 4–6 mg/ml.

32. The process of claim 31, where the benzyl alcohol is diluted with water to a concentration of about 2.0%, acid or base is weak HCl or NaOH and the benzyl alcohol is adjusted to a final concentration of between about 1.6 to 1.7% (16–17 mg/ml).

33. The process of claim 26 where the pH of the benzyl alcohol water solution is adjusted to between 6 and 7 before it is mixed with the dinoprost tromethamine in water solution.

* * * * *